United States Patent [19]

Reinert

[11] 4,242,210

[45] Dec. 30, 1980

[54] PROCESS OF PREPARING A FINISHING COMPOSITION CONTAINING AZIRIDINE RADICALS USED FOR REDUCING THE SHRINKAGE AND FELTING OF WOOD

[75] Inventor: Friedrich Reinert, Wachenheim, Fed. Rep. of Germany

[73] Assignee: BASF Aktiengesellschaft, Fed. Rep. of Germany

[21] Appl. No.: 38,849

[22] Filed: May 14, 1979

[30] Foreign Application Priority Data

Jun. 3, 1978 [DE] Fed. Rep. of Germany ....... 2824469

[51] Int. Cl.³ ................. D06M 13/48; D06M 15/52; D08G 65/00

[52] U.S. Cl. ...................................... 252/8.8; 252/8.9; 260/239 E

[58] Field of Search ................................ 252/8.9, 8.8

[56] References Cited

FOREIGN PATENT DOCUMENTS 1470243 4/1977 United Kingdom .

*Primary Examiner*—Joseph L. Schofer
*Assistant Examiner*—Herbert J. Lilling
*Attorney, Agent, or Firm*—Keil & Witherspoon

[57] ABSTRACT

British Pat. No. 1,470,243 relates to aziridine compounds suitable for finishing wool, but the method of formulation, described there, of these compounds for practical purposes proved unsatisfactory. This problem is solved by the present invention.

5 Claims, No Drawings

PROCESS OF PREPARING A FINISHING COMPOSITION CONTAINING AZIRIDINE RADICALS USED FOR REDUCING THE SHRINKAGE AND FELTING OF WOOD

The present invention relates to an improved process for the formulation of compounds of the general formula I, ie. for their conversion into a form suitable for use.

British Pat. No. 1,470,243 relates to compounds containing aziridine radicals, of the general formula I

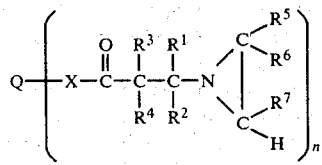

where $R^1$ to $R^7$ are hydrogen or low molecular weight alkyl, Q is the radical of an n-hydric alcohol or phenol, n is 2 or 3 and X is a polyether chain of butoxy and/or propoxy units, with or without ethoxy units, which chain has an atomic ratio C:O of not less than 2.67:1 and a molecular weight of from 150 to 1,500 if $n=2$ and from 150 to 3,000 if $n=3$, and to a process for reducing the shrinkage and felting of wool by means of such compounds.

The type of formulation described there is relatively expensive; it requires intensive stirring and relatively large amounts of emulsifier, which impair the hand of the finished textile, make it undesirably hydrophilic and increase the ease of soiling. Furthermore, in the case of the formulation according to the above British Patent, application by the exhaustion process presents problems.

It is an object of the present invention to provide an improved process for the formulation of the finishing agents according to the said British Patent, which process in particular overcomes the said disadvantages.

We have found that this object is achieved by providing the process defined in the claims.

The surfactants used are adducts of alcohols of 8 to 18 carbon atoms with from 5 to 80, preferably from 10 to 30, moles of ethylene oxide and/or adducts of alkylphenols, where alkyl is of 8 to 12 carbon atoms, with from 5 to 80, preferably from 7 to 20, moles of ethylene oxide, the hydrophilic radical, ie. the number of ethylene oxide molecules which have undergone adduct formation, being in each case in a suitably balanced ratio to the size of the hydrophobic radical. If, at a low degree of oxyethylation, the emulsifying action is insufficient, it can be improved by adding other emulsifiers, for example an adduct of p-benzyl-o-phenylphenol with about 10 moles of ethylene oxide. Particularly preferred surfactants are the adducts of from 10 to 20 moles of ethylene oxide with aliphatic alcohols of 10 to 14 carbon atoms and of from 7 to 20, especially of from 9 to 15, moles of ethylene oxide with nonylphenol. The lower limit of the amount of ethylene oxide to be used advantageously in forming the adduct is imposed by the emulsifying action of the surfactants, ie. the stability of the emulsions. The upper limit follows from the decreasing solubility in the active compound, or active compound solution. The same criteria also determine the limits of the amounts of surfactant advantageously to be employed. These limits are from 2 to 20, preferably from 6 to 14, percent by weight, based on active compound (formula I).

"Dilute aqueous acid" means an aqueous solution of any organic or inorganic acid, having a pH of from about 1 to 5. Depending on the content of basic impurities (for example calcium oxide), in the main originating from the process of manufacture, in the active compound, and depending on the concentration of the aqueous acid, a greater or lesser amount of acid, as a rule from about an equal amount to twice the amount by weight of 1 N acid, based on active compound, is required to obtain a clear solution. In view of the danger of aziridine ring cleavage it is advisable not to employ an unnecessarily large amount of acid and to neutralize the acidic solution immediately after it has been produced and the nonionic surfactant has been added. The nature of the acid is immaterial. Examples are water-soluble aliphatic monocarboxylic and dicarboxylic acids of 1 to 6 carbon atoms, preferably formic acid and acetic acid, and the industrially most important inorganic acids, ie. hydrochloric acid, sulfuric acid and phosphoric acid.

The active compound can be dissolved directly in the aqueous acid. However, it is simpler and therefore more advantageous first to dilute the active compound with from 10 to 1,000, preferably from 30 to 200, especially from 50 to 100, percent by weight of a water-miscible solvent which boils below 160° C., preferably below 100° C. Examples are methanol, ethanol, propanol, i-propanol, i-butanol, acetone, methyl ethyl ketone and N-methylpyrrolidone. Tetrahydrofuran, however, has been found to be less suitable. As a result of the dilution with the solvent, the active compound, which in the pure form is generally pasty, can be handled more easily and dissolves more rapidly in the aqueous acid.

The sequence in which the surfactant and active compound or active compound solution are added to the aqueous acid is immaterial. It has proved expedient to dissolve the surfactant in the solution of active compound before adding this solution to the acid. As a rule, this method furthermore does not require the use of particularly intensive stirring. As soon as a clear acidic aqueous solution has been obtained, the pH is brought to from 5 to 10, preferably from 7 to 9, by adding aqueous ammonia solution. If the wool to be finished has been treated beforehand with an oxidizing agent and/or chlorinating agent, a pH of from 6 to 8 (instead of from 7 to 9) is preferred for the finishing liquor. The ammonia solution should be dilute so that no precipitate is formed. If it is desired to use a fairly concentrated ammonia solution, it is necessary to stir intensively whilst adding the ammonia. In principle, any other alkalis can also be used, but ammonia has the particular advantage that the ammonium salts formed, in contrast to the salts of strong bases, catalyze the subsequent fixing of the active compound to wool. It is true that amine salts would also exhibit this effect, but amines would not offer any advantage over ammonia and would be more expensive.

The finishing agents are now no longer in the form of a solution but of an emulsion. The emulsions are translucent. The higher the pH, the more milky the emulsion. The shelf life increases with increasing pH and at pH 8–9 is of the order of magnitude of several days to several weeks.

Finally, the solution is diluted to the desired concentration, which depends on the amount which it is intended to apply, and on the wet pick-up. Of course, other materials, for example other finishing agents, catalysts, for example sodium bisulfite or ammonium bisulfite, and other assistants can be added to the liquor.

It is a surprising aspect of the formulation process according to the invention that the aziridine radicals, which are generally reputed to be acid-sensitive, withstand this method of treatment without loss of activity, and that surfactants have been found which prevent flocculation of the finishing agent when the pH of the treatment bath is raised, but do not detract from the non-felting effect.

The advantages of this novel process over that described in the above British Patent in which the compounds containing aziridine groups and dissolved in a water-immiscible solvent are emulsified directly by means of an emulsifier system are, inter alia, that the preparation of the treatment liquors is substantially simplified, since the solution of the active compound in the organic solvent can be directly dissolved in acidified water, without using a stirrer, that the amount of emulsifier used is substantially reduced, so that the finished textile is less hydrophilic and has a better hand, that the range of possible applications is extended, since finishing can be carried out by the exhaustion method, which is not possible with the relatively coarse emulsions obtained according to the process of the above British patent, that the wet soiling and dry soiling characteristics of the treated wool are improved since the finish contains less of surfactants which have a softening effect, and that the non-felting effect is improved as a result of the finishing agent being distributed more finely over the textile.

In the Examples which follow, parts and percentages are by weight; in the case of data relating to wet pick-up and amounts applied to the fibers, the percentages are based on the weight of the dry fiber material. The relaxation shrinkage and felting shrinkage are shown in the Tables as the percentage shrinkage in area of the test specimen.

EXAMPLE 1

47 g (a) or 71 g (b) of a mixture of 50 parts of polytetrahydrofuran-2,000 bis-$\beta$-aziridinopropionic acid ester (active compound), 5 parts of a polyadduct of 14 moles of ethylene oxide (EO) with 1 mole of nonylphenol and 45 parts of isopropanol are stirred into 47 g or 71 g of 10 percent strength acetic acid and the mixture is made up to about 800 ml with water. After it has been neutralized with dilute ammonia and 70 g/l of a 10 percent strength ammonium bisulfite solution have been added, the mixture is made up to 1 liter and the pH of the finishing bath is brought to 7–8.

Two lengths of an undyed double-knit jersey of pure new wool weighing 300 g/m² are impregnated with these liquors, squeezed off to 85% wet pick-up on a padder, stretched to the initial width on a pin tenter and dried for 8 minutes at 130° C. in a through-circulation dryer.

The finished samples are washed, together with a non-finished comparative sample, for 3 hours at 40° C. in a Cubex machine. The wash test corresponds to Specification IWS/TM 185 of the International Wool Secretariat. The results are shown in Table 1.

TABLE 1

| Example | Amount of active compound g/l | in % | Relaxation shrinkage | Felting shrinkage |
|---|---|---|---|---|
| 1a | 23.5 | 2 | 6.4 | 7.8 |
| 1b | 35.5 | 3 | 4.6 | 3.8 |
| Comparative sample | 0 | 0 | 15 | 38 |

EXAMPLE 2

Sizable pieces of a carded wool fabric and of a worsted fabric are treated with liquors which contain 67 or 10% of the mixture of active compound, surfactant and i-propanol described in Example 1. The batches are formulated as described in Example 1 except that the amount of acetic acid is 6.7 and 10%, respectively, of the amount of liquor. The fabrics are impregnated, and squeezed off to a wet pick-up of 60%, on a padder. They are then dried on a tenter with 12% overfeed, at 130° C. and a speed of 5 m per minute. The non-felting effect is determined by the IWS test method, as in Example 1. The results on the finished samples and on the non-finished comparative samples are shown in Table 2.

TABLE 2

| Sample | Amount of active compound g/l | in % | Relaxation shrinkage | Felting shrinkage |
|---|---|---|---|---|
| Worsted (comparative experiment) | 0 | 0 | 5.2 | 49 |
| Worsted | 50 | 3 | 3.6 | 5.3 |
| Carded wool (comparative experiment) | 0 | 0 | 10.2 | 30 |
| Garded wool | 33.5 | 2 | 0.3 | 3.6 |

EXAMPLE 3

The conditions for this Example are as in Example 1, except that 71 g of the stated mixture are stirred into
 (a) 71 g of 10 percent strength acetic acid
 (b) 3 g of glacial acetic acid
 (c) 142 g of 1 N formic acid
 (d) 142 g of 1 N maleic acid
 (e) 142 g of 1 N hydrochloric acid
 (f) 142 g of 1 N sulfuric acid
 (g) 142 g of 1 N phosphoric acid Thereafter the formulation is carried out as in Example 1. The test specimens, of DIN A4 size, are washed for 3 hours at 40° C. in 12 l of a liquor which contains 2 g of a detergent for delicate fabrics. Table 3 shows the results on the treated samples and on a untreated comparative sample.

TABLE 3

| Example | Total shrinkage |
|---|---|
| 3a | 11 |
| 3b | 10 |
| 3c | 9 |
| 3d | 11 |
| 3e | 10 |
| 3f | 11 |
| 3g | 9 |

TABLE 3-continued

| Example | Total shrinkage |
| --- | --- |
| Comparative sample | 49 |

EXAMPLE 4

The conditions for this Example are as in Example 1, except that 36 g of active compound and 3.6 g of surfactant are mixed with the following water-miscible solvents:
 (a) no solvent
 (b) 3.6 g of isopropanol
 (c) 36 g of isopropanol
 (d) 108 g of isopropanol
 (e) 36 g of methanol
 (f) 36 g of acetone
 (g) 36 g of methyl ethyl ketone
 (h) 36 g of N-methylpyrrolidone Using the method described in Example 1, the finishing liquors are prepared and the lengths of fabric are finished and dried. The test specimens are washed in a washing machine, as described in Example 3. The results are shown in Table 4.

TABLE 4

| Example | Total shrinkage |
| --- | --- |
| 4a | 9 |
| 4b | 8 |
| 4c | 9 |
| 4d | 8 |
| 4e | 8 |
| 4f | 9 |
| 4g | 9 |
| 4h | 9 |

In the case of Example 4a it proved necessary to stir the 39.6 g of mixture of active compound and surfactant very carefully with the acid if a clear solution was to be obtained. If instead of the 10 percent strength acetic acid, 3 g of glacial acetic acid are used, the active compound solution dissolves substantially more easily, and the use of a solvent is unnecessary.

EXAMPLE 5

The conditions for this Example are as in Example 1, except that the concentration of the polyadduct of 14 moles of EO with 1 mole of nonylphenyl is 2% (a) or 20% (b), based on active compound. The wash test is carried out as stated in Example 3. The results are shown in Table 5.

EXAMPLE 6

The conditions for this Example are as in Example 1, except that in place of the surfactant used in Example 1 (a polyadduct of 14 moles of EO with 1 mole of nonylphenol), 3.6 g (10%, based on active compound) of an adduct of 8 moles of EO (a) or 20 moles of EO (b) with 1 mole of nonylphenol are employed. The results of the washing machine test are shown in Table 5.

EXAMPLE 7

The conditions for this Example are as in Example 1, except that 3.6 g of an adduct of octylphenol with 25 moles of EO (a) or with 50 moles of EO (b) are used. The area shrinkage on washing in the washing machine is shown in Table 5.

EXAMPLE 8

The conditions for this Example are as in Example 1, except that 3.6 g of an adduct of a $C_{12-14}$-alcohol with 7 EO (a), of a $C_{9-11}$-alcohol with 30 EO (b) or of a $C_{12-18}$-alcohol with 80 EO (c) are employed. The results are shown in Table 5.

EXAMPLE 9

The conditions for this Example are as in Example 1, but in addition 10%, based on active compound, of an adduct of p-benzyl-o-phenylphenol with 10 moles of EO are added to the active compound mixture. In this way, very stable, almost water-clear finishing liquors are obtained. The results are shown in Table 5.

TABLE 5

| Example No. | Total shrinkage |
| --- | --- |
| 5a | 8 |
| 5b | 9 |
| 6a | 10 |
| 6b | 10 |
| 7a | 9 |
| 7b | 10 |
| 8a | 9 |
| 8b | 10 |
| 8c | 10 |
| 9 | 8 |

EXAMPLE 10

8 kg of the undyed double jersey used in Example 1 are treated for about 1 hour at 20°–25° C., on a pilot-plant winch vat, in 400 l of a liquor, containing 80 g of an emulsified triisobutyl phosphate as the wetting agent and 160 g of the sodium salt of dichloroisocyanuric acid (active chlorine content 56%). The pH is brought to 4.8 with acetic acid, 160 g of sodium disulfite are then added and the material is dechlorinated for 20 minutes at 30° C. After rinsing, the fabric is dried on a tenter at 100° C.

The fabric is then treated with the finishing bath described in Example 1, in the same way as described in Example 1 except that the amount of active compound and amount of acetic acid are 23.5 and 35 g, respectively. The area shrinkage of the Cubex-washed fabric is shown in Table 6.

TABLE 6

| Amount of active compound | | Relaxation shrinkage | Washing shrinkage |
| --- | --- | --- | --- |
| g/l | in % | | |
| 11.8 | 1 | 6.3 | 1.9 |
| 17.5 | 1.5 | 6.1 | 1.2 |

EXAMPLE 11

110 kg of 100% wool tops are treated in a top dyer for 5 minutes at 20° C. with 1.2 m³ of a liquor which contains 1.1 kg of emulsified triisobutyl phosphate as the wetting agent and 1.2 l of 60% strength acetic acid. Thereafter, 3.3 kg of the sodium salt of dichloroisocyanurate (DCCA) are added and the pH is brought to 4.8 with acetic acid. The liquor is pumped for 10 minutes in the inward direction and for 10 minutes in the outward direction. Thereafter it is pumped for 15 minutes in the outward direction whilst being heated to 35° C. Finally, dechlorination is carried out with 1.1 kg of sodium disulfite, the pH is brought to 6 with ammonia solution and the tops are dyed in the conventional manner with wool dyes. A sample of the tops treated in this way is dried, to provide a comparative sample for the subsequent felting test; the main part of the tops is treated as follows in a backwasher:

1st bath: 400 l of cold water containing 200 g of an adduct of nonylphenol with 7 moles of ethylene oxide; feed 0.2%, based on the dry weight of the tops passing through the bath.

2nd bath: cold water, pH brought to 5 with acetic acid.

3rd bath: 4 kg of the mixture of active compound, surfactant and isopropanol, described in Example 1, are mixed with 4 kg of 10% strength acetic acid, and the mixture is diluted with water to 350 l, brought to a pH of 6 with dilute ammonia solution and made up to 400 l with water.

Feed: 10%, based on the dry weight of the wet tops passing through the bath, of an aqueous solution, prepared in accordance with the above formulation and containing 100 g/l of the 50% strength active compound solution.

4th bath: rinse with cold water.

The tops are dried at 70°–80° C.

To assess the finishing effect, the specimen of tops is stitched into cotton poplin and, using a modified version of the IWS test method TM 185, is allowed to relax in 15 liters of liquor at 25° C. in the large Cubex apparatus for 55 minutes under static conditions and for 5 minutes with agitation. It is then washed for 3 hours at room temperature (about 25° C.). Thereafter, the length of the tops specimen is measured. The reduction in length is expressed as a percentage. The results are shown in Table 7.

EXAMPLE 12

Wet woollen tops (dry weight 200 kg) which have been dyed in the conventional manner in a dyeing machine are impregnated with water in a horizontal pad and squeezed off thoroughly, so that the remaining wet pick-up is only 55%. The tops are then impregnated, in a second horizontal paid with a liquor, at 20° C., which contains 120 g/l of the sodium salt of dichloroisocyanuric acid and 10 g/l of an adduct of a $C_{9-10}$-oxo-alcohol with 5 moles of ethylene oxide, and are squeezed off to a wet pick-up of 80%. After a 3 minute dwell at 20° C., the tops are treated with the following baths in a lisseuse:

1st bath: 400 l of cold water containing 8 kg of sodium disulfite, and 800 ml of 60% strength acetic acid.

Feed: 2% of sodium disulfite (based on the dry weight of the wet tops passing through the bath).

2nd bath: cold water, pH brought to 5 with acetic acid.

3rd bath: as for the 3rd bath in Example 11

4th bath: cold water

The tops are dried at 70°–80° C.

The felting characteristics are tested as described in Example 11. The results are shown in Table 7.

EXAMPLE 13

5 kg of wool tops are impregnated with 35 g/l of the sodium salt of dichloroisocyanurate and with 10 g/l of an adduct of a $C_{9-10}$-oxo-alcohol with 5 moles of ethylene oxide, and squeezed off to a wet pick-up of 100%, on a horizontal pad. Thereafter, 10 g/l of sodium disulfite are added for dechlorination, and the tops are rinsed with cold water, these operations being carried out in succession and on the same padder as used for the impregnation. The chlorine-treated tops are transferred to a pilot-plant dyeing machine, dyed in the conventional manner with wool dyes and rinsed. 60 l of fresh cold liquor are then brought to pH 9 with ammonia. A solution of 75 g of the active compound mixture described in Example 1, 75 g of 10% strength acetic acid and 7.5 g of an adduct of p-benzyl-o-phenylphenol with 10 moles of ethylene oxide are added to this liquor, and the pH is brought to 8 with ammonia. When the liquor has been circulated for 10 minutes, dilute acetic acid is added slowly, so that after 20 minutes pH 5 is reached. The dyeing cycle is 2 minutes with the liquor circulating outwards and 5 minutes with it circulating inwards. The liquor is drained off and the wool is taken out and dried. The results of the non-felting finishing treatment of the samples (which were tested as described in Example 11) are shown in Table 7.

TABLE 7

| Example | Amount of DCCA in % | Amount of active compound in % | Felting shrinkage |
|---|---|---|---|
| Comparative experiment | 3 | — | 40 |
| 11 | 3 | 0.5* | 5 |
| Comparative experiment | 3 | — | 36 |
| 12 | 3 | 0.5* | 2 |
| Comparative experiment | 3.5 | — | 30 |
| 13 | 3.5 | 1.5 | 3 |

*The amount of active compound absorbed corresponds to the feed.

I claim:

1. A process for preparing a finishing agent for reducing the shrinkage and felting of wool which comprises: dissolving (a) a compound of the formula I $$\left\{Q-X-\overset{O}{\underset{\|}{C}}-\underset{R^4}{\overset{R^3}{\underset{|}{C}}}-\underset{R^2}{\overset{R^1}{\underset{|}{C}}}-N\underset{C\diagdown H}{\overset{C-R^5}{\diagup R^6}}_{R^7}\right\}_n$$

where $R^1$ to $R^7$ are hydrogen or low molecular weight alkyl, Q is the radical of an n-hydric alcohol or phenol, n is 2 or 3 and X is a polyether chain of butoxy and/or propoxy units, with or without ethoxy units, which chain has an atomic ratio C:O of not less than 2.67:1 and a molecular weight of from 150 to 1,500 if n=2 and from 150 to 3,000 if n=3, and (b) from 2 to 20 percent by weight, based on said compound I, of an adduct of an alcohol of 8 to 18 carbon atoms with from 5 to 80 moles of ethylene oxide in sufficient dilute aqueous acid to give an optically clear solution, and thereafter adding aqueous ammonia solution to the solution to bring the pH of the solution to from 5 to 10.

2. The process of claim 1, wherein the compound of the formula I, before being dissolved in aqueous acid, is dissolved in from 0.1 to 10 times its amount by weight of a water-miscible solvent having a boiling point of less than 160° C.

3. The process of claim 2, wherein an alcohol of 1 to 3 carbon atoms is employed as the water-miscible solvent.

4. The process of claim 1 wherein the amount of said adduct is from 6 to 14 percent by weight, based on said compound I.

5. The process of claim 1 wherein the pH of the solution is brought to from 7 to 9 by the addition of an aqueous ammonia solution.

* * * * *